United States Patent [19]
Chen et al.

[11] Patent Number: 5,654,005
[45] Date of Patent: Aug. 5, 1997

[54] CONTROLLED RELEASE FORMULATION HAVING A PREFORMED PASSAGEWAY

[75] Inventors: Chih-Ming Chen, Davie; Der-Yang Lee, Plantation; Jianbo Xie, Davie; Aurelio Rodriguez, Hialeah, all of Fla.

[73] Assignee: Andrx Pharmaceuticals, Inc., Fort Lauderdale, Fla.

[21] Appl. No.: 476,455

[22] Filed: Jun. 7, 1995

[51] Int. Cl.⁶ .................. A61K 9/22; A61K 9/36
[52] U.S. Cl. ............... 424/480; 424/468; 424/473
[58] Field of Search .................. 424/468, 473, 424/480

[56] References Cited

U.S. PATENT DOCUMENTS 4,783,337  11/1988  Wong et al. .................. 424/468

*Primary Examiner*—Thurman K. Page
*Assistant Examiner*—James M. Spear
*Attorney, Agent, or Firm*—Hedman, Gibson & Costigan, P.C.

[57] ABSTRACT

A controlled release pharmaceutical tablet having at least one passageway, said tablet having:
  (a) a compressed core which comprises:
    (i) a medicament;
    (ii) an amount of a water soluble osmotic agent which is effective to cause the medicament to be delivered from said passageway in the presence of aqueous media;
    (iii) a water-swellable pharmaceutically acceptable polymer; and
  (b) a membrane coating around said core tablet which comprises a water insoluble pharmaceutically acceptable polymer.

14 Claims, 3 Drawing Sheets

CONTROLLED RELEASE FORMULATION HAVING A PREFORMED PASSAGEWAY

BACKGROUND OF THE INVENTION

The present invention relates to a novel orally administrable controlled release unit dose formulation for the administration of pharmaceuticals. In the prior art many techniques have been used to provide controlled and extended release pharmaceutical dosage forms in order to maintain therapeutic serum levels of medicaments and to minimize the effects of missed doses of drugs caused by a lack of patient compliance.

Certain prior art extended release tablets containing osmotic tablets have been described and manufactured which have had an osmotically active drug core which expands when contacted with gastric fluids and extrudes out a separate layer that contains an active drug. The core is divided into two layers one of which contains the active drug and the other contains a push layer of pharmacologically inactive ingredients which are osmotically active in the presence of gastrointestinal fluids. These tablets are provided with an aperture that is formed by punching or drilling a hole in the surface using a mechanical or laser drilling apparatus. A product of this type is disclosed in U.S. Pat. No. 4,783,337 and is sold commercially as Procardia XL®.

The osmotic dosage forms that are disclosed in U.S. Pat. No. 4,783,337 are described as having a passageway which includes an aperture, orifice, hole, porous element, hollow fiber, capillary tube, microporous insert, pore, microporous overlay or bore which extends through the semipermeable lamina, the microporous lamina, or through the laminated wall. The patent also states that the passageway may be formed by mechanical drilling, laser drilling, eroding an erodible element, extracting, dissolving, bursting or leaching a passageway-former from the wall of the osmotic dosage form (col. 14, line 35 et seq.) which are implicitly preformed in the tablet during the manufacturing process. The only exemplified technique of forming a passageway in U.S. Pat. No. 4,783,337 is the use of a laser to drill a hole in the outer layer of the tablet.

U.S. Pat. No. 4,285,987 described an osmotic tablet which had a laser drilled aperture into the core of the tablet. The laser drilled hole was plugged with leachable sorbitol which was leached out in the presence of gastrointestinal fluid.

The present invention is concerned with providing an osmotic tablet having an aperture but does not have a separate "push" layer in the core which contains no medicament. In addition, a coating process has been invented which applies an insoluble coating to a tablet having an aperture without causing the aperture to become coated or clogged by the coating.

SUMMARY OF THE INVENTION

The present invention is directed to a controlled release pharmaceutical tablet having at least one passageway which extends from the outside surface into the core, said tablet comprising:
(a) a compressed core which comprises:
  (i) a medicament;
  (ii) an amount of a water soluble osmotic agent which is effective to cause the medicament to be delivered from said passageway in the presence of aqueous media;
  (iii) a water-swellable pharmaceutically acceptable polymer; and
(b) a membrane coating around said core tablet which comprises a water insoluble pharmaceutically acceptable polymer.

It is an object of the invention to provide a a controlled release pharmaceutical tablet having an aperture which extends from the outside surface of said tablet into an osmotic core which is covered with a external polymeric membrane.

It is also an object of the invention to provide a dosage formulation that provides therapeutic blood levels with once a day administration.

It is also an object of the present invention to provide a controlled release pharmaceutical tablet that has a water insoluble coating on the exterior surface and no coating on the pre-formed aperture which extends from the exterior surface of the tablet into the core of said tablet.

It is also an object of this invention to provide a controlled release pharmaceutical tablet having a single component osmotic core wherein the core component may be made using ordinary tablet compression techniques.

These and other objects of the invention will become apparent from the appended specification.

DETAILED DESCRIPTION OF THE INVENTION

Figure 1:
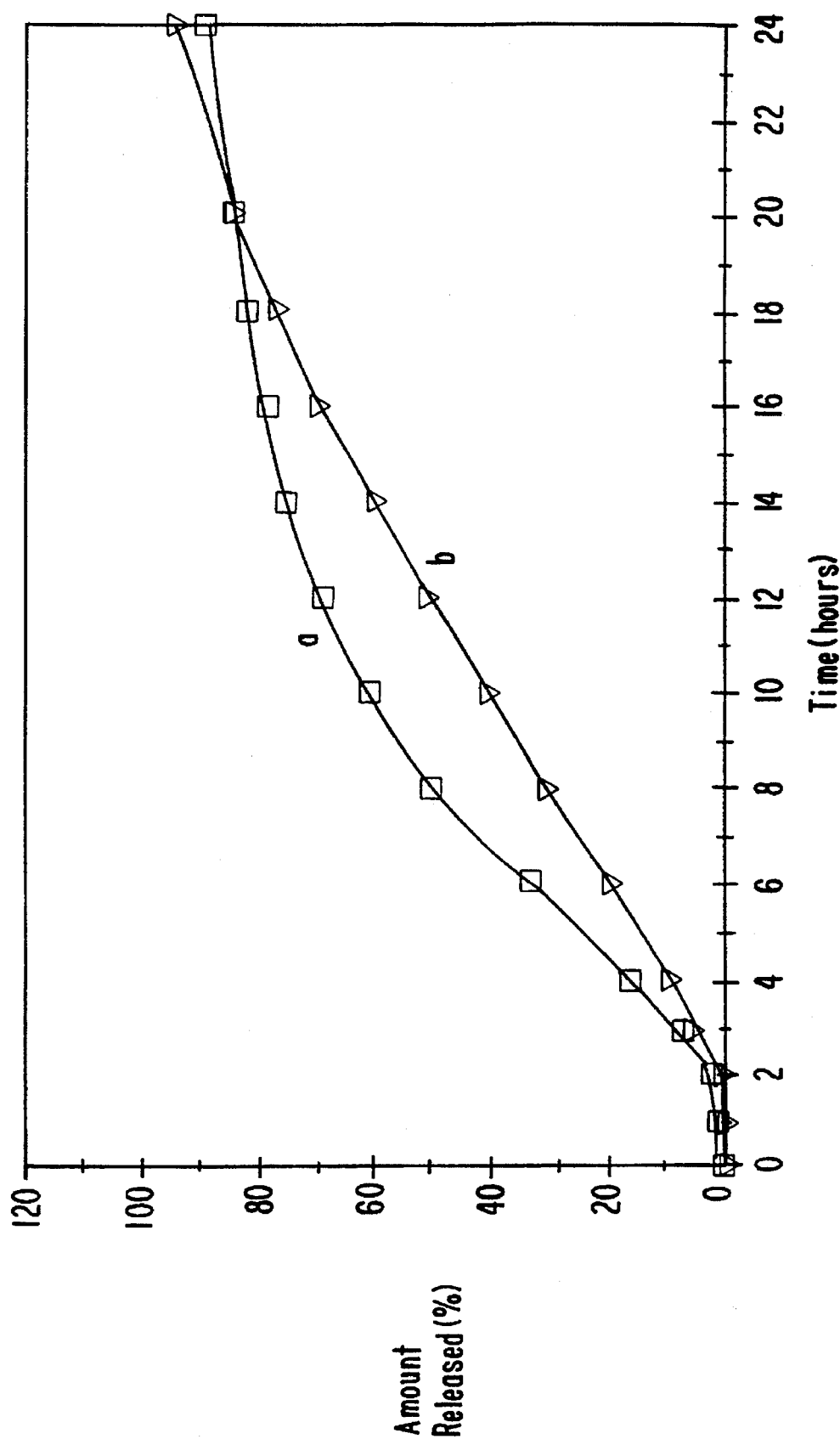
FIG. 1 is a graph which compares the in vitro release rate, in 0.25 wt. % sodium lauryl sulfate, of a nifedipine tablet prepared according to Example 1 of the present application (a), with the commercial product Procardia XL® (b).

The controlled release osmotic tablet formulation of the invention provides performance which is equivalent to much more complicated prior art controlled release dosage formulations which require a complex segmented osmotic core and an aperture which is formed after a water insoluble coating is applied to the core.

The core of the controlled release tablet of the present invention may be made by direct compression of the core components or by initially forming granules by combining a medicament and a water soluble osmotic agent with conventional excipients and a water soluble polymeric binder. Thereafter, the granules are blended with a water swellable polymer and suitable excipients to form a composition which may be compressed into tablets. A tabletting machine is used to compress the core forming components into a core tablet which is subsequently coated with a water insoluble polymeric membrane to form the controlled release tablet of the invention. The passageway may be formed before or after the water insoluble polymeric membrane is placed on the tablet.

The water insoluble coating is applied to tablets which have a preformed aperture. The coating technique comprises the use of a fluidized bed coater in which a water insoluble resin is applied as a dispersion or solution in a highly volatile organic solvent. It has been found that using the proper residence time in a particular type of a fluidized bed coater with a properly selected solvent, the coating will not be deposited within the preformed aperture of the tablet in such a manner that the release of the drug from the core will be affected by coating.

Although the inventor does not wish to be bound by any theory by which the present invention operates, it is believed that the application of the water insoluble polymer, to form the external membrane around the core of the tablet, does not coat the interior walls of the aperture of the tablet or cause the outer opening of the aperture to become clogged because the coating solution has a low viscosity and is applied under fluidized bed coating conditions where the finely divided or atomized coating solution volatilizes before any liquid coating solution penetrates into the aperture of the tablet. When the tablet is placed in an aqueous medium, water is taken up through the passageway and into the core of the tablet, the water swellable polymer expands as the water soluble osmotic agent dissolves and increases the osmotic pressure inside the tablet causing the core component to extrude out of the tablet via the passageway.

The controlled release tablet of the invention is intended to be used to administer medicaments which are water soluble to practically insoluble in water. The term practically insoluble is used to include those substances which are soluble at a level of 1 of solute to from 100 to more than 10,000 parts of water per part of solute. The term water soluble includes those substances which are soluble at level of one part of solute to 5 parts of water or less.

Examples of categories of water insoluble medicaments which may be utilized, at therapeutic dose levels, in the controlled release tablets of the invention include anti-hypertensives, calcium channel blockers, analgesics, anti-neoplastic agents, anti-microbials, anti-malarials, non-steroidal anti-inflammatory agents, diuretics, anti-arrythmia agents, hypoglycemic agents and the like. Specific examples of medicaments include nifedipine, nisoldipine, nicardipine, nilvadipine, felodipine, bendroflumethazide, acetazolamide, methazolamide, chlorpropamide, methotrexate, allopurinol, erythromycin, hydrocortisone, triamcinolone, prednisone, prednisolone, norgestrel, norethindone, progesterone, norgesterone, ibuprofen, atenolol, timolol, cimetidine, clonidine, diclofenac, glipizide, and the like. Useful water soluble medicaments include various therapeutic agents such as decongestants, antihistamines, analgesics, sedatives, anti-inflammatory, anti-depressants, antihypertensives and the like at therapeutic dosage levels.

Examples of specific medicaments which may be utilized, at therapeutic dose levels, in the controlled release tablets of the invention include ephedrine, pseudoephedrine, phenylpropanolamine, chlorpheniramine, diphenhydramine, dimenhydramine, indomethacin, labetalol, albuterol, haloperidol, amitriptyline, clofenac, clonidine, terfenadine, fentanyl, and the like which are in the form of a water soluble salt such as the hydrochloride or sodium salt or in the from of an ester, ether, amide, complex or the like.

The water soluble osmotic agent is any non-toxic pharmaceutically acceptable compound which will dissolve sufficiently in water and increase the osmotic pressure inside of the core of the tablet. The osmotic agents are used in effective amounts, which are from 5 to 55% by weight of the total weight of the core, and preferably from 10 to 50% by weight of the total weight of the core tablet. When the drug is water soluble, lesser amounts of the osmotic agent will be employed. These osmotic agents include sodium chloride, potassium chloride, magnesium sulfate, magnesium chloride, sodium sulfate, lithium sulfate, urea, inositol, sucrose, lactose, glucose, sorbitol, fructose, mannitol, dextrose, magnesium succinate, potassium acid phosphate and the like as well as osmopolymers such as polyethylene oxide having a weight average molecular weight of 50,000 to 300,000; polyvinyl pyrrolidone and the like.

If granules are prepared a binder may be optionally employed. The binders include any pharmaceutically acceptable material which can be utilized to bind the powder mixture together with an adhesive, instead of by compaction, in order to form granules for making compressed tablets. These polymers include polyvinyl pyrrolidone, carboxyvinyl polymer, methylcellulose, hydroxyethylcellulose, hydroxypropylcellulose, low molecular weight polyethylene oxide polymers, hydroxypropylmethylcellulose, dextrin, maltodextrin and the like. These materials may be used as a dry solid binder or formed into a dispersion or solution in water or other solvent system at a sufficient concentration to have a binding effect on the osmotic agent, the medicament and any excipient.

Generally the binder is used in a sufficient amount so that when it is combined with a suitable solvent, combined with the water soluble osmotic agent and agitated, granules will be formed which may be compressed into a tablet core. If a binder is used, it should be used at a level of 5 to 15 wt % based on the total weight of the core components.

Prior to compressing the granules, a water swellable polymer and one or more conventional pharmaceutical diluents may be added such as microcrystalline cellulose, lactose, dextrose and the like are added to the granule forming mixture in an amount which will aid in forming granules which are compressible to form a tablet core. Generally, if a diluent is added, it will be added at a level which ranges from about 5 to 50 wt % based on the weight of the compressed core.

Suitable pharmaceutically acceptable, water swellable polymers include polyethylene oxide having a molecular weight of 100,000 to 8,000,000; poly(hydroxy alkyl methacrylate) having a molecular weight of from 30,000 to 5,000,000; poly(vinyl) alcohol, having a low acetal residue, which is cross-linked with glyoxal, formaldehyde or glutaraldehyde and having a degree of polymerization of from 200 to 30,000; a mixture of methyl cellulose, cross-linked agar and carboxymethyl cellulose; a water insoluble, water swellable copolymer produced by forming a dispersion of a finely divided copolymer of maleic anhydride with styrene, ethylene, propylene, butylene or isobutylene cross-linked with from 0.001 to 0.5 moles of saturated cross-linking agent of saturated cross-linking agent per mole of maleic anhydride in the copolymer; Carbopol® carbomer which is as acidic carboxy polymer having a molecular weight of 450,000 to 4,000,000; Cyanamer® polyacrylamides; cross-linked water swellable indene-maleic anhydride polymers; Goodrich® polyacrylic acid having a molecular weight of 80,000 to 200,000; starch graft copolymers; Aqua-Keeps® acrylate polymer polysaccharides composed of condensed glucose units such as diester cross-linked polyglucan and the like; Amberlite® ion exchange resins; Explotab® sodium starch glycolate; and Ac-Di-Sol® croscarmellose sodium. Other polymers which form hydrogels are described in U.S. Pat. No. 3,865,108; U.S. Pat. No. 4,002,173 and U.S. Pat. No. 4,207,893 all of which are incorporated by reference. The pharmaceutically acceptable, water swellable polymers may be employed in an effective amount that will control the swelling of the tablet core. These amounts will generally be from about 3 to 12 wt %, preferably from about 5 to 10 wt % based on the weight of the compressed tablet core.

The membrane coating around said core consists essentially of a plasticized or unplasticized water insoluble pharmaceutically acceptable polymer. Suitable water insoluble polymers include cellulose esters, cellulose ethers and cellulose esterethers. The cellulosic polymers have a degree of substitution greater than 0 up to 3. The degree of substitution is calculated as the average number of original hydroxyl groups on the anhydroglucose unit which makes up the cellulose polymer which are replaced with a substitute group. These materials include cellulose acylate, cellulose ethyl ether, cellulose diacylate, cellulose triacylate, cellulose acetate, cellulose diacetate, cellulose triacetate, mono-, di- and tricellulose alkan, mono-, di- and tricellulose aroyl and the like. Cellulose triacetate is the preferred polymer. Other water insoluble polymers are disclosed in U.S. Pat. No. 4,765,989 which is incorporated by reference. If desired other polymers may be combined with the water insoluble polymer to modify the permeability of the membrane coating around the core. These include hydroxymethyl cellulose, hydroxypropyl cellulose or cellulose per se. Generally, the membrane coating around the core will comprise from about 4 to 12 wt % preferably about 6 to 10 wt % based on the total weight of the core tablet.

The water insoluble polymer may optionally contain a plasticizer or a water soluble channeling agent. The water soluble channeling agent is a material that dissolves in water to form a porous polymer shell that allows water to be imbibed into the core. This material is used in a sufficient amount that channels will form in the water insoluble polymer. These materials include water soluble organic and inorganic compounds such as sucrose, lactose, dextrose, sodium chloride, sorbic acid, potassium chloride, polyethylene glycol (weight av. molecular weight 380–420), propylene glycol; hydroxypropyl methylcellulose, hydroxypropyl cellulose, polyvinylpyrrolidone and mixtures thereof.

The water insoluble polymer may be plasticized with a plasticizing amount of a plasticizer. The preferred plasticizer is triacetin but materials such as acetylated monoglyceride, rape oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, and the like. Depending on the particular plasticizer or water soluble channeling agent, amounts of from 1% to 40%, and preferably 10 to 30% of the modifier based on the total weight of the water insoluble polymer, water soluble polymer and the modifier may be utilized.

In the preparation of the tablets of the invention, various conventional well known solvents may be used to prepare the granules and apply the external coating to the tablets of the invention. In addition, various diluents, excipients, lubricants, dyes, pigments, dispersants etc. which are disclosed in Remington's Pharmaceutical Sciences, 1985 Edition may be used to optimize the formulations of the invention.

Generally the depth of the aperture should be from twice the thickness of the coating layer to two-thirds of the thickness of the tablet. The aperture may be sized to be from 0.2 to 3.0 mm. in diameter and from 0.2 to 3 mm. in depth. If desired, the passageway may be extended all of the way through the tablet. The passageway may be formed by punching or drilling the passageway using a mechanical or laser apparatus or using a properly sized projection on the interior of the tablet punch to form the passageway. A preferred manner of forming the passageway is by the use of a cylindrical or frustroconical pin which is integral with the inside surface of the upper punch of the punch which is used to form the tablet.

For certain applications, it may be desirable to add a further coating layer over the water insoluble membrane coating for the purpose of providing an immediate release drug layer for the purpose of providing an initial loading or therapeutic dose of a drug. The drug in such an immediate release layer may be the same or different from the drug which is placed in the core of the tablet. A example of an immediate release coating, which may be placed on the outer membrane of the tablet which is disclosed in Example 3, is as follows:

| Immediate release coating | |
|---|---|
| pseudoephedrine HCl | 81.1 wt % |
| hydroxylpropyl cellulose, NF (Klucel ® EF) | 13.5 wt % |
| polysorbate 80 | 5.4 wt % |
| water* | (the weight of water is equal to the weight of the tablets) |

*water is evaporated during the coating process

The immediate release coating is applied to the tablets by coating the tablets with the immediate release coating solution. The coating is applied using a fluid bed coater or a perforated coating pan until the tablets exhibit a weight gain of 19.8%.

DESCRIPTION OF THE PREFERRED EMBODIMENTS

EXAMPLE 1

Tablets having the following formula are prepared as follows:

| I Core Tablet: | |
|---|---|
| nifedpine | 12 wt % |
| polyethylene oxide[1] | 10% wt % |
| polyethylene oxide[2] | 20% wt % |
| sodium starch glycolate | 30 wt % |
| lactose, NF | 27 wt % |
| magnesium stearate | 1 wt % |

[1]Polyox WSR 303; weight average molecular weight = 7,000,000;
[2]Polyox WSR N80; weight average molecular weight = 200,000;

(a) The nifedipine, the polyethylene oxides, the sodium starch glycolate and the lactose are dry blended for 15 minutes and then mixed with the magnesium stearate for an additional 5 minutes. The powder mixture was then directly compressed into 0.3438" round tablets (275 mg) with a 1.3 mm hole (2.5 mm deep) in the center of the tablet using a specially designed upper punch having a cylindrically shaped projection which forms the hole in the tablet.
II Sustained release coating Core tablets weighing a total of 300 g were then coated in a Glatt fluidized bed coating apparatus with the following coating composition:

| | |
|---|---|
| cellulose acetate | 80 wt % |
| polyethylene glycol 400 | 5 wt % |
| sugar, confectioner's 6X (micronized) | 10 wt % |
| triacetin | 5 wt % |
| acetone* | (10 times the weight of the coating materials) |

The coating conditions for this batch are as follows: spraying rate: 6 ml/min.; inlet temperature: 24°–28° C.; atomization pressure: 1 bar. The coating procedure is carried out until a weight gain of 7.5% is obtained. The coated tablets were dried in the fluidized bed apparatus for an additional 5 minutes at 28° C. *The acetone is evaporated during the coating process The dissolution profiles of the coated tablets and Procardia XL® in 0.25% sodium lauryl sulfate, in a USP Type 2, paddle apparatus, at 100 rpm and 37° C. are set forth in FIG. 1.

EXAMPLE 2

Tablets having the following formula are prepared as follows:

| I Core Tablet | |
| --- | --- |
| glipzide | 4 wt % |
| polyethylene oxide[1] | 10% wt % |
| polyethylene oxide[2] | 20% wt % |
| sodium starch glycolate | 30 wt % |
| hydroxypropyl methylcellulose | 10 wt % |
| lactose, NF | 34 wt % |
| magnesium stearate | 1 wt % |

[1]Polyox WSR 303; weight average molecular weight = 7,000,000;
[2]Polyox WSR N80; weight average molecular weight = 200,000;

(a) The glipzide, polyethylene oxides, sodium starch glycolate, hydroxypropylmethylcellulose and the lactose were mixed for 15 minutes and were then mixed with the magnesium stearate for an additional 5 minutes. The powder mixture was compressed into the same size tablets having the same passageway as the tablets described in Example 1. The tablets were then coated using the same procedure and coating suspension that was used to coat the tablets of Example 1.

Figure 2:
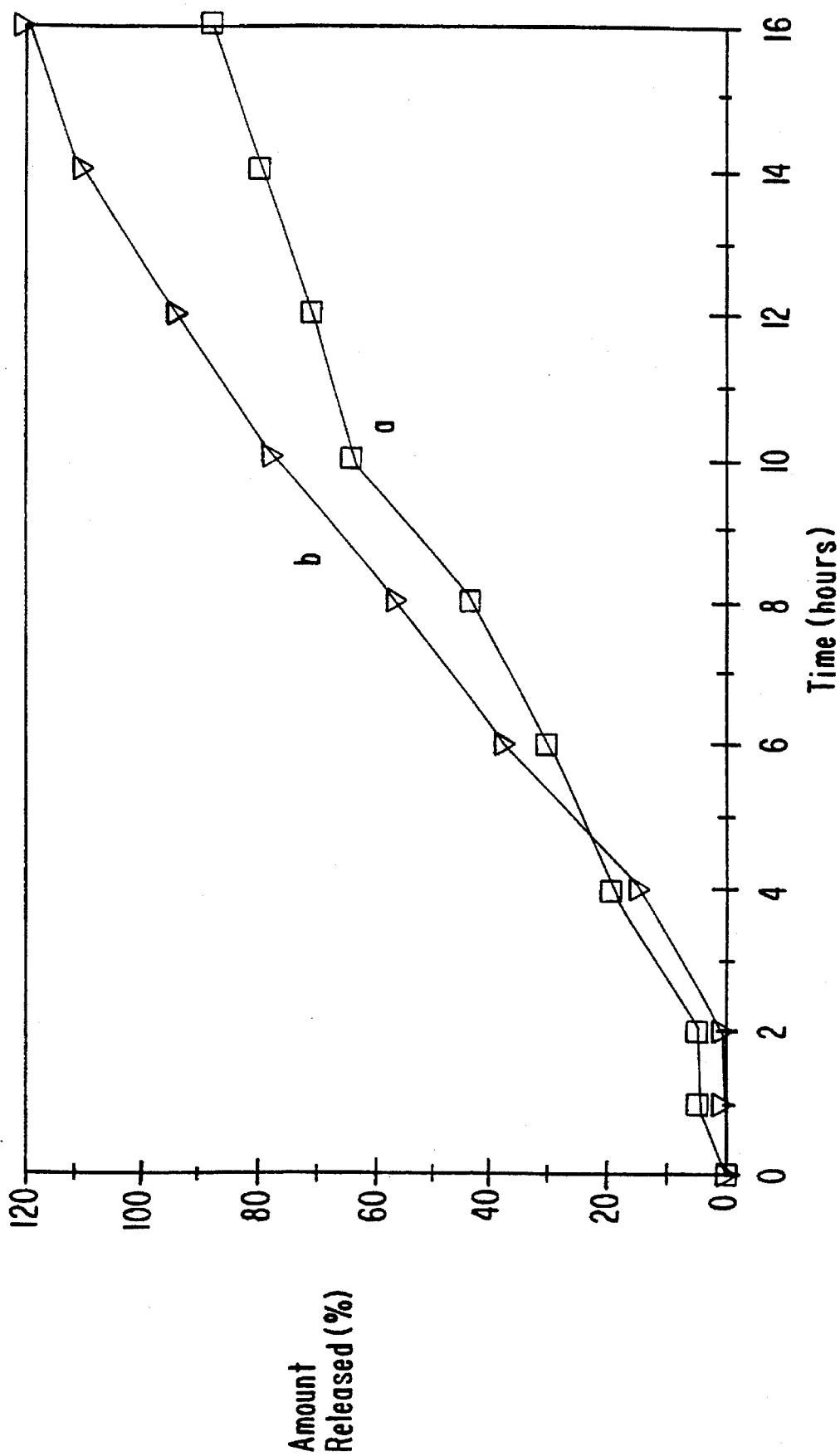
FIG. 2 is a graph which compares the in vitro release rate, in simulated intestinal fluid, of a glipizide tablet prepared according to Example 2 of the present application (a), with the commercial product Glucotrol XL® (b).
Figure 3:
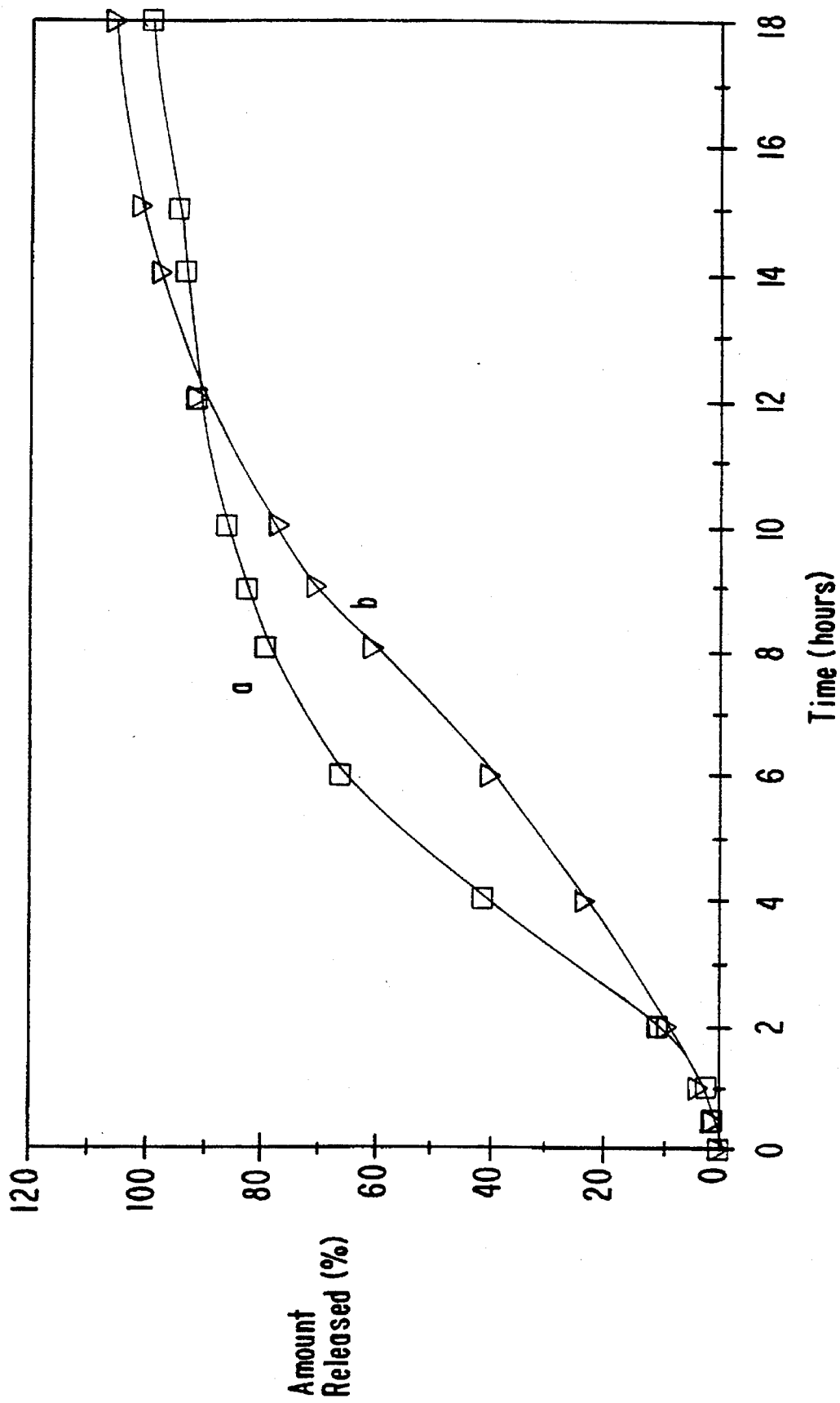
FIG. 3 is a graph which compares the in vitro release rate, in distilled water, of a pseudoephedrine HCl core containing 180 mg of pseudoephedrine HCl which was prepared according to Example 3 of the present application (a), with the commercial product Efidac/24® (b) which was modified by washing off the immediate release layer.

The dissolution profiles of the tablets of Example 2 are shown on FIG. 2.

EXAMPLE 3

A tablet having the following formula is prepared:

| I Granulation | |
| --- | --- |
| pseudoephedrine HCl | 74.80 wt % |
| microcrystalline cellulose, NF | 10.27 wt % |
| sodium chloride, USP powder | 9.73 wt % |
| povidone[1], USP | 5.20 wt % |
| purified water* | (10 times the amount of povidone) |

[1]weight average molecular weight = 55,000; freely soluble in water (1 g in 1–10 ml of water); dynamic viscosity (10% w/v solution at 20° C.) = 5.5–8.5 m Pa s
*water is evaporated during the granulation process.

(a) The povidone is dissolved in water to make a 10 wt. % solution. Then the pseudoephedrine hydrochloride, sodium chloride and microcrystalline cellulose are mixed and placed in a granulator and the povidone solution is sprayed onto the mixture to form granules. The drying cycle is initiated after the granulation process is completed. The drying cycle is continued until the moisture loss on drying (LOD) is not more than 2.0% at about 50° C. Then, the dry granules are sized with a 40 mesh (USS) screen in an oscillating granulator.

| II Tabletting | Case I | Case II |
| --- | --- | --- |
| granules (from I) | 79 wt % | 89 wt % |
| polyethylene oxide[2] | 20 wt % | 10 wt % |
| magnesium stearate | 1.0 wt % | 1.0 wt % |

[2]Polyox WSR 303; weight average mol. wt. 7,000,000

(b) A tablet core is made by adding the polyethylene oxide and the magnesium stearate to the granules prepared in step (a). Core tablets weighing 305 mg each for Case I and 271 mg each for Case II are prepared using a tablet press machine using 0.3438" standard concave punches with a projection as described in Example 1 in the upper punch.

The core tablets were then coated according to the procedure of Example 1.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

We claim:

1. A controlled release pharmaceutical tablet having at least one passageway, said tablet comprising:
   (a) a compressed core which consists essentially of:
      (i) a medicament;
      (ii) an amount of a water soluble osmotic agent which is effective to cause the medicament to be delivered from said passageway in the presence of aqueous media;
      (iii) a water-swellable pharmaceutically acceptable polymer comprising poly(ethylene oxide) having a weight average molecular weight of 100,000 to 8,000,000; and
   (b) a membrane coating around said core tablet which comprises a water insoluble pharmaceutically acceptable polymer.

2. A controlled release pharmaceutical tablet as defined in claim 1 wherein the medicament is selected from the group consisting of anti-hypertensives, calcium channel blockers, analgesics, anti-neoplastic agents, anti-microbials, anti-malarials, non-steroidal anti-inflammatory agents, diuretics, decongestants, antihistamines, analgesics, sedatives, anti-inflammatory agents, anti-depressants, antihypertensives, hypoglycemic agents and anti-arrythmia agents.

3. A controlled release pharmaceutical tablet as defined in claim 1 wherein the water soluble osmotic agent is selected from the group consisting of lactose, sodium chloride, potassium chloride, magnesium sulfate, magnesium chloride, sodium sulfate, lithium sulfate, urea, inositol, sucrose, lactose, glucose, sorbitol, fructose, mannitol, dextrose, magnesium succinate, potassium acid phosphate, poly(ethylene oxide), polyvinylpyrrolidone and mixtures thereof.

4. A controlled release pharmaceutical tablet as defined in claim 1 wherein the water swellable polymer is selected from the group consisting of poly(ethylene oxide), hydroxypropylmethylcellulose and mixtures thereof.

5. A controlled release pharmaceutical tablet as defined in claim 1 wherein the water insoluble polymer in the membrane around the core contains a plasticizer or a channeling agent.

6. A controlled release pharmaceutical tablet as defined in claim 5 wherein the water insoluble polymer in the membrane around the core contains a plasticizer.

7. A controlled release pharmaceutical tablet as defined in claim 1 wherein the water insoluble polymer in the membrane around the core is a water insoluble cellulose.

8. A controlled release pharmaceutical tablet as defined in claim 7 wherein the water insoluble cellulose polymer in the membrane around the core is cellulose acetate.

9. A controlled release pharmaceutical tablet as defined in claim 5 wherein the membrane around the core also includes a channeling agent.

10. A controlled release pharmaceutical tablet which consists essentially of:
   (a) a compressed core which consists essentially of:
      (i) a calcium channel blocker;
      (ii) an amount of a water soluble osmotic agent which is effective to cause the medicament to be delivered from said passageway in the presence of aqueous media;
      (iii) a pharmaceutically acceptable polymer binder;
      (iv) a water-swellable pharmaceutically acceptable polymer which is poly(ethylene oxide) having a weight average molecular weight of 5,000,000 to 8,000,00;
      (v) conventional pharmaceutical excipients; and
   (b) a membrane coating around said core tablet which consists essentially of triacetin plasticized cellulose acetate and polyethylene glycol.

11. A controlled release pharmaceutical tablet having a passageway, said tablet comprising:
   a) a compressed core which consists essentially of:
      (i) a calcium channel blocker;
      (ii) poly(ethylene oxide) having a weight average molecular weight of 50,000 to 300,000;
      (iii) poly(ethylene oxide) having a weight average molecular weight of 5,000,000 to 8,000,000;
   (b) a membrane coating around said core tablet which consists essentially of triacetin, sucrose, cellulose acetate and polyethylene glycol 400.

12. A controlled release pharmaceutical tablet as defined in claim 10 wherein the calcium channel blocker is nifedipine.

13. A controlled release pharmaceutical tablet having an passageway, said tablet comprising:
   (a) a compressed core which consists essentially of
      (i) a decongestant and/or an antihistamine;
      (ii) an amount of a water soluble osmotic agent which is effective to cause the medicament to be delivered from said passageway in the presence of aqueous media;
      (iii) a pharmaceutically acceptable polymer binder;
   (b) a membrane coating around said core tablet which consists essentially of triacetin, sucrose, cellulose acetate and polyethylene glycol 400.

14. A controlled release pharmaceutical tablet as defined in claim 13 which comprises:
   (a) a compressed core which consists essentially of:
      (i) pseudoephedrine hydrochloride and terfenadine, and
      (ii) from 5 to 55% by weight of a water soluble osmotic agent based on the total weight of the compressed core;
      (iii) a pharmaceutically acceptable polymeric binder;
      (iv) a conventional pharmaceutical excipient; and
   (b) a dual membrane coating around said core which consists essentially of:
      (i) a membrane coating around said core tablet which consists essentially of triacetin, sucrose, cellulose acetate and polyethylene glycol 400; and
      (ii) an outer membrane of pseudoephedrine, terfenadine and hydroxypropyl cellulose.

* * * * *